(12) United States Patent
Ikeda et al.

(10) Patent No.: US 12,352,904 B2
(45) Date of Patent: Jul. 8, 2025

(54) ULTRASOUND IMAGING APPARATUS AND SIGNAL PROCESSING METHOD, FOR EFFICIENT DELAY-AND-SUM PROCESSING

(71) Applicant: FUJIFILM Healthcare Corporation, Kashiwa (JP)

(72) Inventors: Teiichiro Ikeda, Chiba (JP); Kenichi Adachi, Chiba (JP); Kazuhiro Amino, Chiba (JP); Masanori Hisatsu, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 185 days.

(21) Appl. No.: 18/097,435

(22) Filed: Jan. 16, 2023

(65) Prior Publication Data
US 2023/0228858 A1    Jul. 20, 2023

(30) Foreign Application Priority Data
Jan. 20, 2022    (JP) .................. 2022-007445

(51) Int. Cl.
*G01S 7/52* (2006.01)
*A61B 8/00* (2006.01)

(52) U.S. Cl.
CPC ......... *G01S 7/52025* (2013.01); *A61B 8/4488* (2013.01)

(58) Field of Classification Search
None
See application file for complete search history.

(56) References Cited

U.S. PATENT DOCUMENTS 6,029,116 A * 2/2000 Wright ............... G01S 15/8988
702/32
6,126,602 A * 10/2000 Savord ............... G01S 15/8925
600/443

(Continued)

FOREIGN PATENT DOCUMENTS

CN    104114099 A    10/2014
JP    S 63-153054 A    6/1988

(Continued)

OTHER PUBLICATIONS

Oct. 8, 2024 Japanese official action (and English-language translation thereof) in connection with Japanese Patent Application No. 2022-007445.

(Continued)

*Primary Examiner* — Jeffrey G Hoekstra
*Assistant Examiner* — Nyrobi Celestine
(74) *Attorney, Agent, or Firm* — Paul Teng

(57) ABSTRACT

Receive signals generated by ultrasound waves propagating in completed manner in a depth direction of a subject, are efficiently subjected to delay-and-sum processing, whereby a higher resolution image is generated with reducing a circuit size. Receive signals outputted from multiple ultrasound probe elements are delayed by predetermined delay amounts in association with the depths of receive focal points, respectively, and the delayed receive signal is branched. The phase of the branched receive signal is shifted by a predetermined phase shift amount to generate a phase-compensated signal, and then the phase-compensated signal is added to the receive signal before branched, thereby generating a beamformed signal.

14 Claims, 14 Drawing Sheets

(56) References Cited

U.S. PATENT DOCUMENTS

| | | | | |
|---|---|---|---|---|
| 2014/0240482 A1* | 8/2014 | Ikeda | .................. | H04N 23/632 |
| | | | | 348/77 |
| 2015/0351720 A1* | 12/2015 | Ikeda | .................. | A61B 8/5207 |
| | | | | 600/447 |
| 2017/0042509 A1* | 2/2017 | Ikeda | .................. | G01N 29/262 |
| 2018/0203103 A1* | 7/2018 | Pellegretti | ........... | G01S 15/8977 |
| 2020/0022682 A1* | 1/2020 | Kaneko | ............... | G01S 15/8927 |
| 2020/0158844 A1* | 5/2020 | Li | ............................ | A61B 8/54 |
| 2021/0295816 A1* | 9/2021 | Kim | ....................... | A61B 8/461 |

FOREIGN PATENT DOCUMENTS

| | | |
|---|---|---|
| JP | H 10-277042 A | 10/1998 |
| JP | 2004-194981 A | 7/2004 |
| JP | 2011-024927 A | 2/2011 |
| JP | 2011-250946 A | 12/2011 |
| WO | WO 2015/025654 | 2/2015 |
| WO | WO 2016/125509 A1 | 8/2016 |

OTHER PUBLICATIONS

Chinese official action dated Apr. 26, 2025 (and English translation thereof) in connection with Chinese Patent Application No. 2022111469737.

* cited by examiner

PRESENT EMBODIMENT

COMPARATIVE EXAMPLE

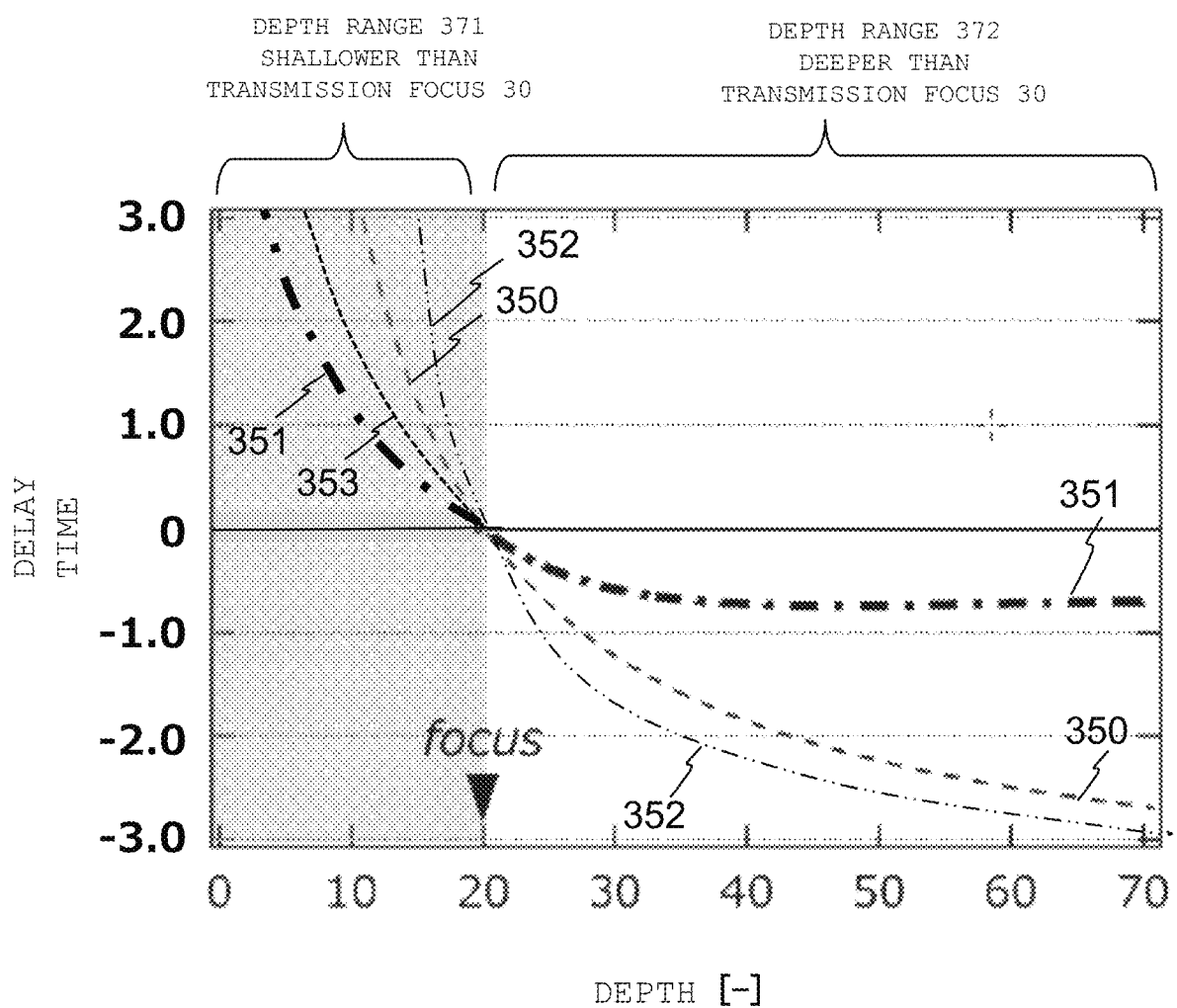

FIG. 14A  IDEAL POINT IMAGE
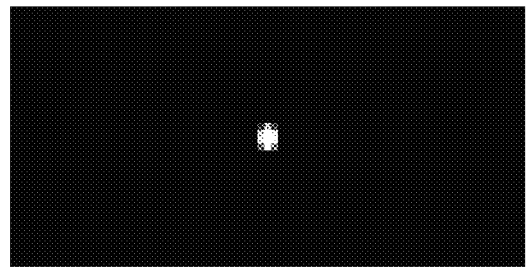
FIG. 14B  COMPARATIVE EXAMPLE (THE NUMBER OF DELAY CURVE IS ONE)
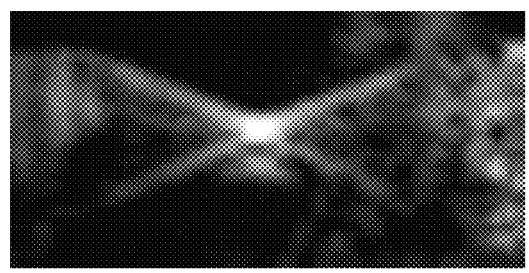
FIG. 14C  FIRST EMBODIMENT (PHASE SHIFT AMOUNT ≤ ONE WAVELENGTH)
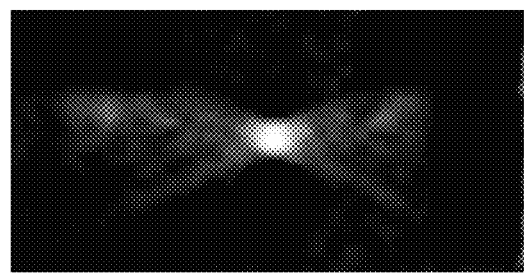
FIG. 14D  FIRST EMBODIMENT (PHASE SHIFT AMOUNT > SEVERAL WAVELENGTHS)
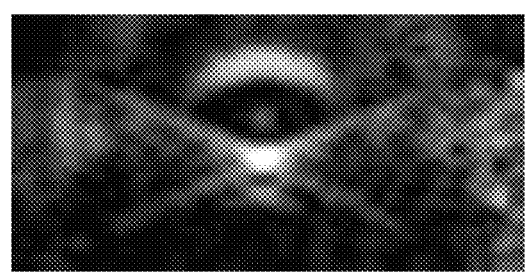
FIG. 14E  FIRST EMBODIMENT (PHASE SHIFT AMOUNT > SEVERAL WAVELENGTHS)
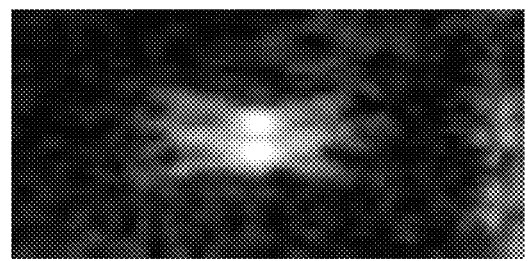

ULTRASOUND IMAGING APPARATUS AND SIGNAL PROCESSING METHOD, FOR EFFICIENT DELAY-AND-SUM PROCESSING

BACKGROUND OF THE INVENTION

Technical Field

The present invention relates to an ultrasound imaging technique of obtaining an image of the inside of a subject body, using ultrasound waves.

Description of the Related Art

Ultrasound imaging is a technique of non-invasively imaging the inside of a subject, including a human body, using ultrasound waves (sound waves not intended to be heard, generally high-frequency sound waves equal to or higher than 20 kHz).

In an ultrasound imaging apparatus, transmission and receive of ultrasound waves are performed by an array of ultrasound probe elements having a finite aperture width, and thus they are influenced by ultrasound diffraction at the edge of the aperture. Accordingly, it is difficult to improve resolution in the azimuthal direction. Therefore, there have been proposed new beamforming schemes such as an adaptive beamformer and synthetic transmit aperture (synthetic aperture).

JP-H10-277042 (hereinafter referred to as Patent Document 1) discloses a technique among ultrasound imaging techniques that perform focused transmission, to perform synthetic transmit aperture beamforming using a method improved from a virtual sound source method. Specifically, in the region where energy of an ultrasound beam converges to a focal point (region A in FIG. 2 of Patent Document 1), the synthetic transmit aperture beamforming is performed, assuming the focal point as a virtual sound source, and in the region where ultrasound energy is diffused around the focal point (regions B and C), the synthetic transmit aperture beamforming is performed assuming that spherical waves are radiated from an end of the probe.

On the other hand, WO2016/125509 (Patent Document 2) discloses an ultrasound imaging apparatus including two or more delay-and-sum units that delay and add receive signals, respectively by two or more types of delay time. The first delay-and-sum unit delays and adds the receive signals, by a first delay time for beamforming the receive signals generated from a transmission beam (interference waves) transmitted from an ultrasound probe element. The second delay-and-sum unit delays and adds, by a second delay time for beamforming the receive signals generated from diffraction waves (spherical waves) having a phase different from that of the transmission beam. Signals after the delay-and-sum, respectively by the first and second delay-and-sum units, are synthesized.

SUMMARY OF THE INVENTION

Technical Problem

In the technique disclosed in Patent Document 1, the synthetic transmit aperture beamforming is performed between transmissions, and thus only one transmission cannot attain a highly precise image.

In the technique of Patent Document 2, the receive signals are added after delayed by two or more types of delay time, respectively. Thus, it is necessary to install two or more delay circuits with respect to one ultrasound probe element, and this increases the circuit size.

An object of the present invention is to efficiently perform delay-and-sum processing on the receive signals being generated by the ultrasound waves propagating in a complicated manner in a depth direction of the subject, so as to generate a higher resolution image, while reducing the circuit size.

Solution to Problem

An ultrasound imaging apparatus of the present invention includes: a transmission beamformer configured to transmit to a subject, an ultrasound wave whose phase is delayed to focus on a predetermined transmission focal point, from each of a plurality of ultrasound probe elements in an ultrasound element array, the ultrasound element array being connected to the ultrasound imaging apparatus; and a receive beamformer configured to perform beamforming on receive signals for each receive focal point provided within the subject and to generate a beamformed signal, the receive signals being received and outputted from the plurality of ultrasound probe elements in the ultrasound element array, after the transmitted ultrasound waves are returned to the ultrasound element array from the subject that received the transmitted ultrasound wave. The receive beamformer includes a delay circuit that delays the receive signals, a summing circuit, and a phase compensation circuit. The delay circuit delays the receive signals outputted from the plurality of ultrasound probe elements, by predetermined delay amounts, respectively in association with the depths of the receive focal point. The summing circuit adds up the receive signals after delayed by the delay circuit and generates the beamformed signal. The phase compensation circuit branches the receive signal delayed by the delayed circuit or the beamformed signal, generates a phase compensation signal obtained by shifting the phase of the receive signal or of the beamformed signal thus branched, by a predetermined phase shift amount, and adds the phase compensation signal to the receive signal or to the beamformed signal thus branched.

According to the present invention, it is possible to provide an apparatus configured to perform efficient delay-and-sum processing, while reducing the circuit size, not only on the transmission beam but also on the receive signals generated by spherical waves that are transmitted from a plurality of ultrasound probe elements and propagating in a depth direction of a subject in a complicated manner, so that a higher resolution image can be generated.

BRIEF DESCRIPTION OF THE DRAWINGS

FIG. 13 is a graph showing an example of the delay curve representing the delay time with respect to the depth according to the fifth embodiment; and FIG. 14A is an image showing an ideal point image, FIG. 14B is an ultrasound image of a comparative example, and FIGS. 14C to 14E are ultrasound images obtained by the ultrasound imaging apparatus according to the first embodiment.

DETAILED DESCRIPTION OF THE PREFERRED EMBODIMENTS

There will be described an ultrasound imaging apparatus according to an embodiment of the present invention.

First Embodiment

Figure 1:
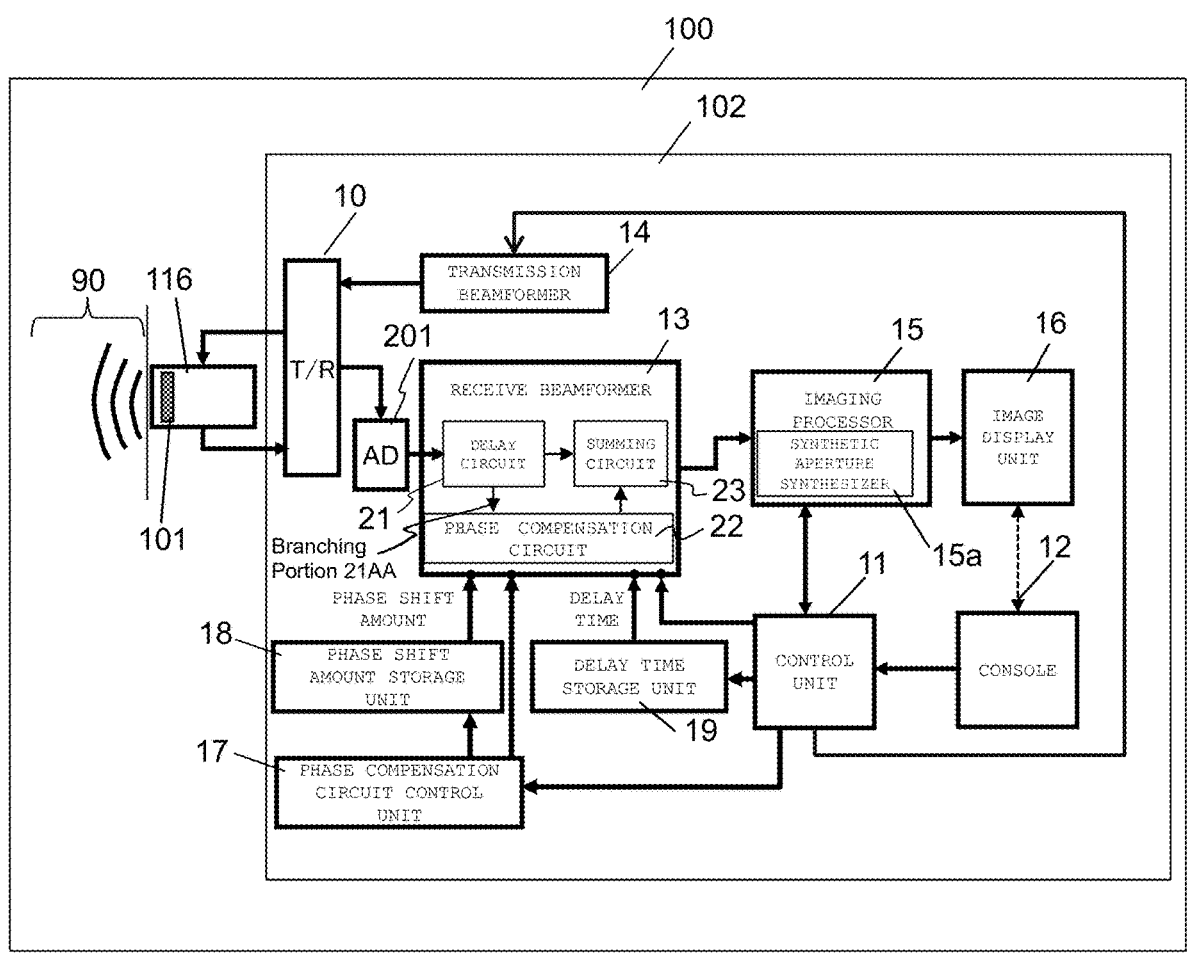
FIG. 1 is a block diagram showing a configuration of an ultrasound imaging apparatus of the first embodiment.
Figure 2A:
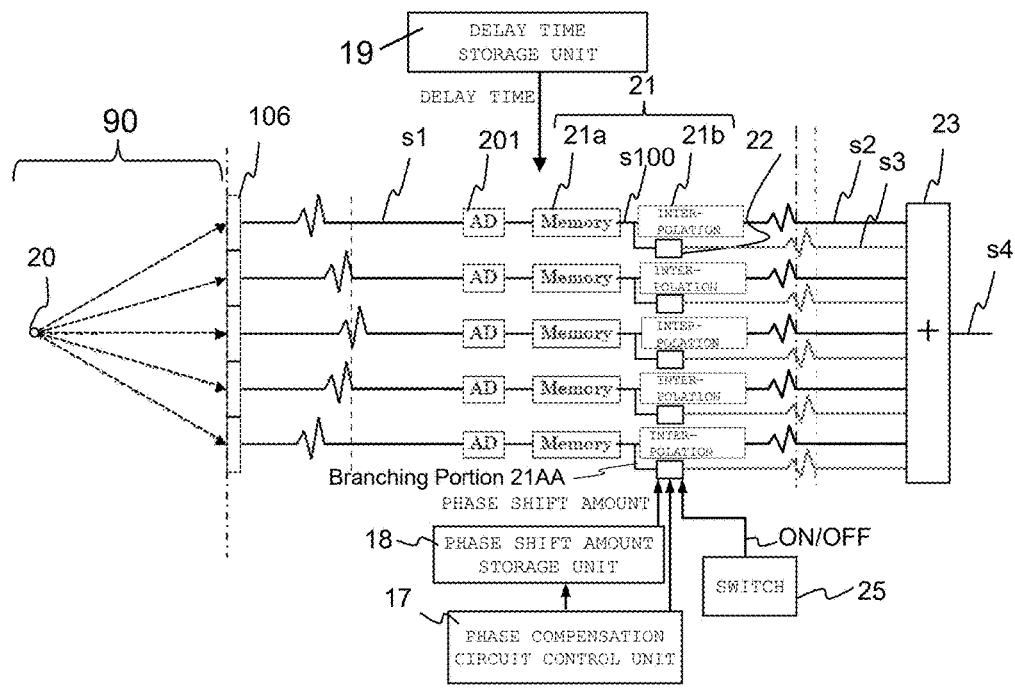
FIG. 2A is block diagram showing a configuration of a receive beamformer of the first embodiment.
Figure 2B:
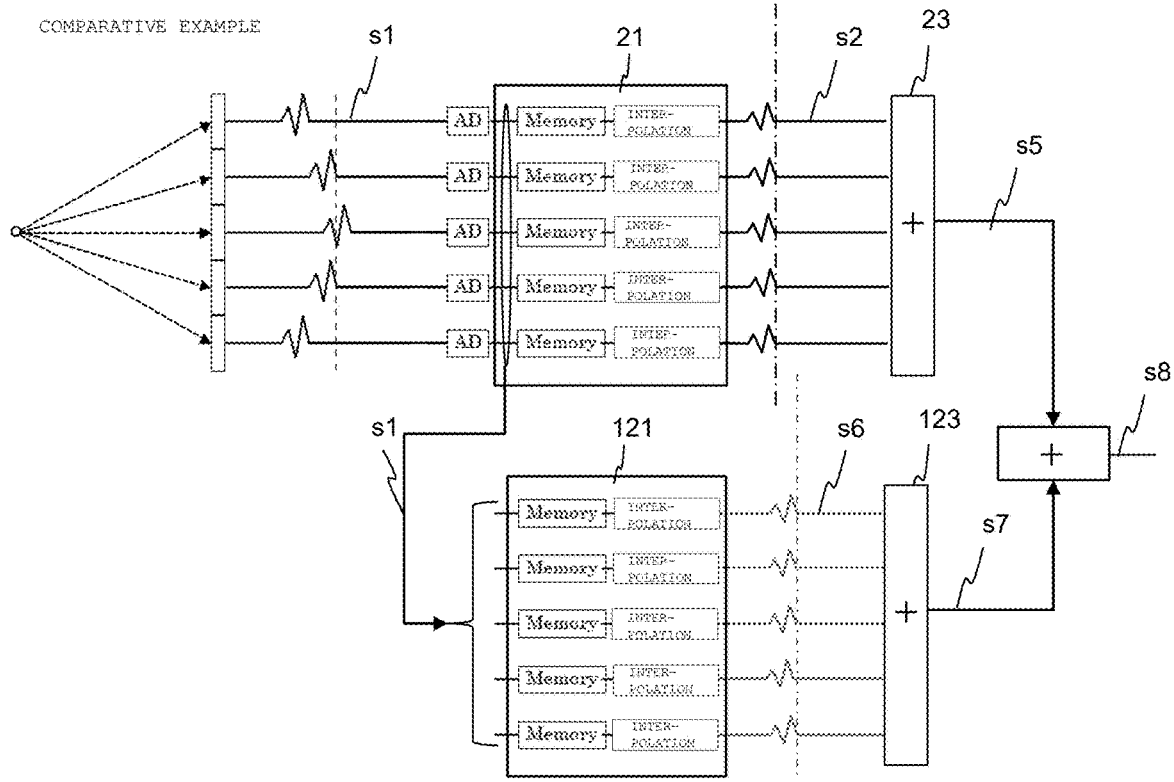
FIG. 2B is a block diagram of the receive beamformer of a comparative example.

First, the ultrasound imaging apparatus 100 of the first embodiment will be described with reference to FIGS. 1 to 6. FIG. 1 illustrates a configuration of an ultrasound diagnostic apparatus, and FIG. 2A illustrates a configuration of the receive beamformer.

As shown in FIG. 1, the ultrasound imaging apparatus 100 of the present embodiment includes, an ultrasound imaging apparatus main body 102, and an ultrasound probe 116 having an ultrasound element array 101, connected to the ultrasound imaging apparatus main body 102. The ultrasound element array 101 has a configuration in which multiple ultrasound probe elements are arranged in an array. The multiple ultrasound probe elements (channels) in the ultrasound element array 101 used for transmission may also be referred to as transmission channels, and multiple ultrasound channels used for receiving may also be referred to as receive channels.

The main part of the ultrasound imaging apparatus main body 102 will be described with reference to FIGS. 1 and 2. The ultrasound imaging apparatus main body 102 includes a transmission beamformer 14, a receive beamformer 13, a phase compensation circuit control unit 17, a phase shift amount storage unit 18, a transmission and receive separating circuit 10, an AD converter 201, an imaging processor 15, a control unit 11, an image display unit 16, and a console 12.

In the present embodiment, the receive beamformer 13 includes a delay circuit 21, a phase compensation circuit 22, and a summing circuit 23.

The receive signal s1 outputted from each of the multiple ultrasound probe elements (receive channel 106) is converted into a digital signal by the AD converter 201. The delay circuit 21 of the receive beamformer 13 delays the receive signal s1, after converted to the digital signal, by a delay time predetermined for each receive channel 106 in accordance with the depth of a receive focal point 20. Specifically, the receive signal s1 is subjected to the delay processing with coarse (low) temporal resolution controlled by the timing read from a memory unit 21a, and to the delay processing with high temporal resolution achieved by an interpolation process according to an interpolation circuit 21b, thereby generating a plurality of delayed receive signals s2. For example, the delay processing is performed with the temporal resolution approximately equal to or higher than a wavelength of sound at the timing read from the memory unit 21a, and then the delay processing is performed with high resolution not more than several times the wavelength of sound according to the interpolation processing by the interpolation circuit 21b.

The phase compensation circuit 22 branches (via branching portion 21AA) one or more receive signals s100 among the plurality of receive signals s100 immediately after being read from the memory unit 21a in the delay circuit 21, and shifts the phase of thus branched one or more receive signals s100 by a predetermined amount, thereby generating a phase-compensated receive signal s3. The amount of phase shift is read out from the phase shift amounts stored in advance in the phase shift amount storage unit 18, respectively associated with the depths of the receive focal point 20, in response to a reading instruction from the phase compensation circuit control unit 17. In the example of FIG. 2A, the phase compensation circuit 22 branches all the receive signals s100 delayed with the coarse temporal resolution that is read from the memory unit 21a in the delay circuit 21, and performs the phase shift on each of the receive signals to generate the phase-compensated receive signal s3.

The summing circuit 23 adds the multiple receive signals s2 each delayed by the delay circuit 21, to the phase-compensated receive signals s3 generated by the phase compensator circuits 22, and then creates a beamformed signal s4.

As described so far, in the present embodiment, the phase of the receive signal s100 immediately after read from the memory unit 21a in the delay circuit 21 is shifted, whereby the receive signals s2 and s3, which are substantially the same as the signals delayed at various types of different delay times, can be generated by one delay circuit 21 and phase compensation circuit 22. Since the phase compensation circuit 22 does not require a reading process from the memory unit 21a, it is possible not only to save the amount of memory for that process, but also to eliminate the need for preparing a physical processing line for the signal processing within the circuit. Therefore, a simpler circuit configuration can be implemented than preparing multiple number of full configurations of the delay circuit 21, the number corresponding to the number of various delay processing. Therefore, while reducing the circuit size, it is possible to achieve an effect substantially the same as in the case where the receive signals generated by the ultrasound waves propagating complicatedly in the depth direction of the subject 90 are subjected to the delay-and-sum processing, using various types of delay time. Accordingly, a high-resolution image can be generated.

Hereinafter, there will be described in detail the ultrasound imaging apparatus 100 of the present embodiment.

The transmission beamformer 14 outputs a transmission signal to each of the plurality of ultrasound probe elements (transmission channels 105) of the ultrasound element array 101 connected to the transmission beamformer. The transmission channel 105 converts the transmission signals into ultrasound waves, and transmits the ultrasound waves to the subject 90.

Figure 3:
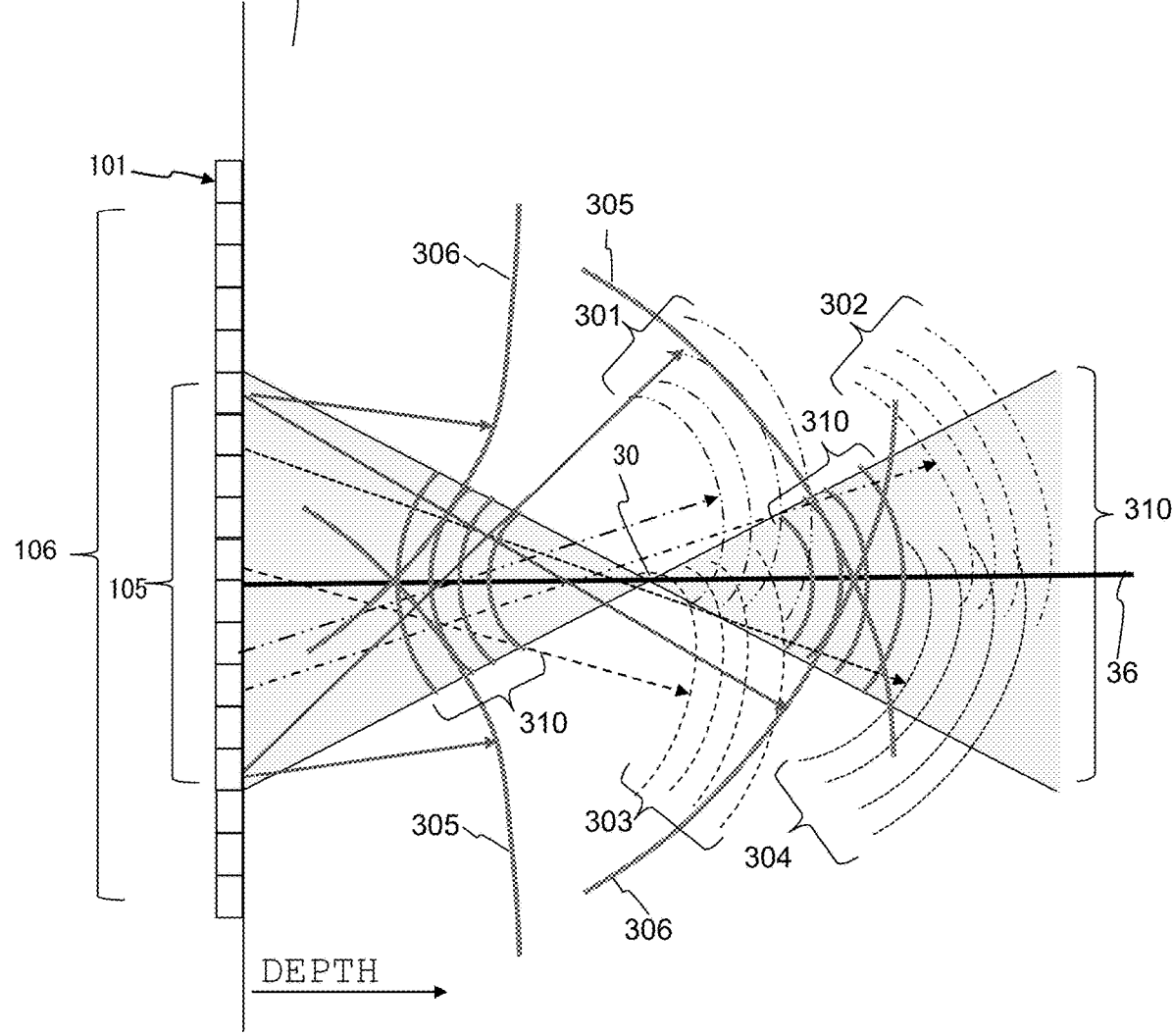
FIG. 3 illustrates the shape and wavefront of the transmission beam 310, and spherical waves thereof.

At this time, the transmission beamformer 14 delays the phase of each transmission signal by a predetermined amount, so that the ultrasound waves (spherical waves) such as the waves 301 to 306 transmitted from the transmission channels 105 interfere with each other and converge at the transmission focus 30 of a predetermined depth as shown in FIG. 3. This allows the subject 90 to be irradiated with a transmission beam (interference wave) 310 that is focused at the transmission focus 30 of a desired depth. As shown in FIG. 3, the ultrasound waves (spherical waves) such as the waves 301 to 306, transmitted from the transmission channels 105 form the above-described transmission beam (interference waves) 310, and in addition, some of the spherical waves such as 301 to 306 propagate with keeping the form thereof, and only a part of which may further interfere with each other to form other interference waves, propagating in the depth direction in a complex manner.

Within the subject 90 where the transmission beam (interference wave) 310, the ultrasound waves (spherical waves) 301 to 306, and other interference waves propagate, these waves are reflected, scattered, or the like, and some of the reflected waves, scattered wave, and others, may again reach the ultrasound element array 101. The waves thus reached are received by the multiple receive channels 106 of the ultrasound element array 101, respectively, and converted into receive signals.

The AD converters 201 convert the receive signals s1 outputted from the receive channels 106, into digital signals, respectively.

As shown in FIG. 2A, the delay circuit 21 of the receive beamformer 13 receives the receive signals s1 from the multiple receive channels 106 via the transmit and receive separating circuit 10 and the AD converters 201, and in accordance with the depth of the receive focal point 20 set in the subject 90, the delay circuit 21 delays each of the receive signals by the delay time indicated by the control unit 11.

Here, the delay circuit 21 includes the memory units 21a and the interpolation circuits 21b, respectively disposed for the receive channels 106.

Each of the memory units 21a once stores the receive signals s1 converted as digital signals.

The interpolation circuit 21b reads the receive signals s100 from the memory unit 21a and performs interpolation processing thereon. At this time, the timing of reading the receive signal s100 from the memory unit 21a is adjusted in the unit of clock (clock frequency) of the digital signal, and the receive signal s1 is delayed with delay accuracy of approximately equal to or more than a wavelength. Next, the interpolation circuit 21b performs the interpolation processing on the readout receive signal s100, and further performs fine delay-time adjustment of equal to or less than the clock frequency, or not more than several times the wavelength. Then, this allows the receive signal s1 to be delayed by the delay-time instructed from the control unit 11, and then delayed receive signal s2 is generated.

The delay time is predetermined according to the distance between the receive focal point 20 and the receive channel 106, and the delay time is stored in the delay time storage unit 19. The control unit 11 provides an instruction for reading the delay time from the delay time storage unit 19, in accordance with the position of the receive focal point 20, and sets the delay time in the delay circuit 21.

The receive signal s2 is obtained by delaying the receive signal s1 outputted from each receive channel 106 by the delay amount in accordance with the distance between the receive focal point 20 and the receive channel 106. Thus, phases of the receive signals s2 are aligned as shown in FIG. 2A.

The phase compensation circuit 22, disposed for each interpolation circuit 21b as shown in FIG. 2A, branches the receive signal s100 immediately after being read from the memory unit 21a in the delay circuit 21, and shifts the phase of thus branched receive signal s1 by a phase shift amount indicated by the phase compensation circuit control unit 17 to generate the phase-compensated receive signal s3.

The phase shift amount is stored in advance in the phase shift amount storage unit 18 in a similar manner as the delay time stored in the delay time storage unit 19, and the phase shift amount is given to the phase compensation circuit 22 in response to an instruction from the phase compensation circuit control unit.

Figure 4:
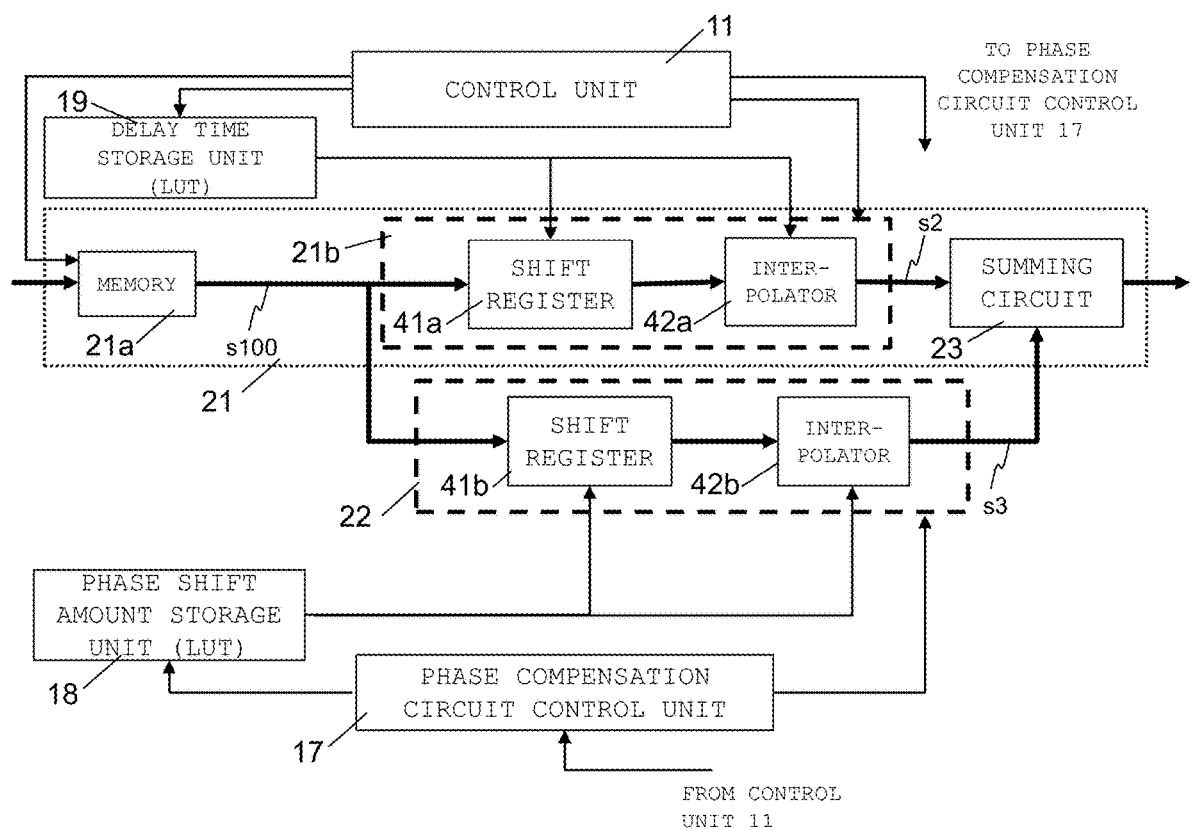
FIG. 4 is a block diagram showing a configuration of the phase compensation circuit of FIG. 1.

With reference to FIG. 4, there will be described specifically the configurations of the interpolation circuit 21b and the phase compensation circuit 22 in the delay circuit 21. First, the interpolation circuit 21b in the delay circuit 21 comprises a shift register 41a and an interpolator 42a. The shift register 41a performs very fine time-shifting and the interpolator 42a performs multiplication by an interpolation coefficient, thereby allowing the receive signal s100 read from the memory to be delayed with a high degree of precision, equal to or less than the clock frequency, or not more than several times the wavelength. The control unit 11 gives an instruction to the interpolation circuit 21b, regarding the read timing received from the memory unit 21a, with referring to a value of LUT (look-up table) stored in the delay time storage unit 19, and provides a time-shift performed by the shift register 41a and the delay time being the interpolation coefficient of the interpolator 42a. This produces the receive signal s2 provided with a delay.

The phase compensation circuit 22 has the same configuration as the interpolation circuit 21b in the delay circuit 21, and comprises the shift register 41b and the interpolator 42b. The receive signal s100 after read from the memory unit 21a is branched, and the shift register 41b and the interpolator 42b in the phase compensation circuit 22 subject the receive signal to a highly precise phase shift, equal to or less than the clock frequency, or not more than several times the wavelength. Here, the amount of the phase shift performed by the phase compensation circuit 22 is stored in advance in the phase shift amount storage unit (LUT) 18 for each depth of the receive focal point. The phase shift amount storage unit 18 sends the amount of phase shift to the phase compensation circuit 22 in accordance with a command read from the phase compensation circuit control unit 17. The phase compensation circuit control unit 17 further sends to the phase compensation circuit 22 control signals such as timing. Then, the phase compensation circuit 22 generates the phase-compensated receive signals s3.

The summing circuit 23 adds the receive signal s2 outputted from the interpolation circuits 21b of the delay circuit 21, being obtained by delaying the receive signal from each of the receive channels 106, to the receive signal s3 outputted from the phase compensation circuits 22, being obtained by performing the phase shift on the receive signal s2, thereby generating the beamformed signal s4.

As shown in FIG. 4, the summing circuit 23 may be configured as adding the receive signals s2 to the receive signals s3 with respect to each channel, and thereafter, summing up between all the channels, the signals after added in each channel. Alternatively, as shown in FIG. 2A, it may be configured as adding the receive signals s2 and the receive signals s3 in all the channels simultaneously.

Thus, by adding the receive signals s2 after delayed, to the receive signals s3 obtained by performing the phase shift on the receive signals s2, it is possible to generate a beamformed signal, not only from the receive signals generated by the transmission beam 310, but also from the receive signals generated from the waves propagating in the form of spherical waves such as the waves 301 to 306, or from the interference waves where some of the spherical waves are interfering. This will be described below.

The delay time storage unit 19 stores the delay time used when the receive beamformer 13 delays the receive signal s1, for each ultrasound probe element (receive channel 106). Since the receive beamformer 13 sequentially obtains focus on a plurality of receive focal points 20 on the receive scanning line set by the control unit 11, this delay time is different depending on the distance between the receive focal point 20 and the receive channel 106. For example, as indicated by the broken line curve 350 in FIG. 5, it varies with the depth of the receive focal point 20. Here, the change of delay time for each depth is also referred as a delay curve.

In the present embodiment, the beamformed signal is generated not only from the receive signals generated by the transmission beam 310, but also from the receive signals generated from the waves propagating in the form of spherical waves such as the waves 301 to 306, or from the interference waves where some of the spherical waves are interfering, the signal (receive signal s2) can be generated by the phase shift of the receive signal s1, this receive signal s2 corresponding to the receive signal obtained by delaying the receive signal s1 at a delay time 351 that is different from the delay time 350 used for focusing the receive signal generated by the transmission beam 310 to the receive focal point 20.

Figure 5:
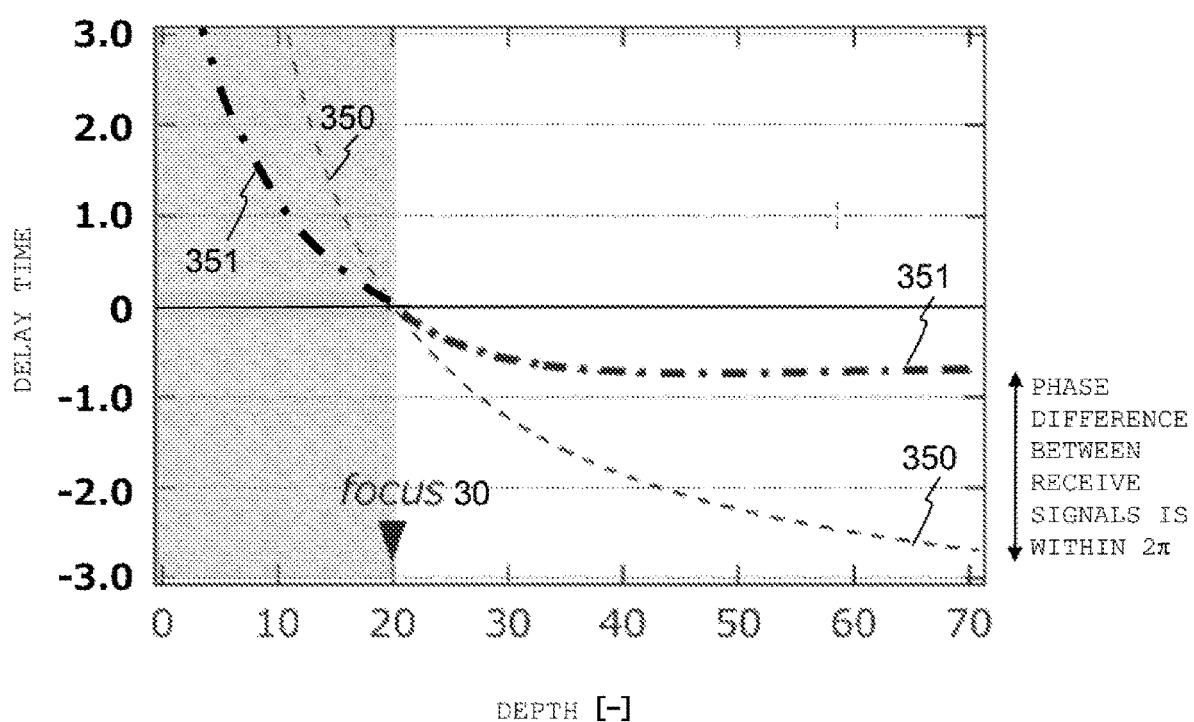
FIG. 5 is a graph showing an example of a delay curve representing the delay time with respect to the depth according to the first embodiment.

For example, as in FIG. 5, the delay time for focusing the receive signal generated by the transmission beam 310 to the receive focal point 20 is the transmission-beam delay time 350, and the delay time required for focusing the receive signal of the reflected wave generated by the spherical wave 301 to the receive focal point 20 is the spherical-wave delay time 351. In that case as in FIG. 2B, it is necessary to prepare another set of the delay circuit 121 and the summing circuit 123, in order that the receive signal s1 is delayed by the spherical-wave delay time 351 and thereafter added to obtain the beamformed signal s7. Then, it is also required to branch the receive signals s1 from the receive channel 106, to delay the receive signal by the spherical-wave delay time 351 according to the other set of the delay circuit 121, added up by the summing circuit 123, and then to obtain receive signals s6.

The inventors have found that the receive signal s6 delayed by the spherical-wave delay time 351 does not have a large phase difference with respect to the receive signal s2 delayed by the transmission-beam delay time 350, and the phase difference falls within one wavelength ($2\pi$ rad). In particular, the followings have been found; the spherical waves themselves transmitted from the channels have a phase difference of one wavelength or more as a whole. However, when the signal delayed by the delay time for the transmission beam is added to the signal delayed by the delay time for spherical waves as in the present invention, if the addition is performed at a phase difference of one or more wavelengths, degradation of resolution due to the phase shift between each other becomes dominant, resulting in that this degradation of resolution hampers enhanced effects of image quality improvement. Therefore, the inventors have suggested a configuration that using the signal s100 immediately after a coarse delay time is imparted when reading from the memory, the phase difference from the receive signal s2 after delayed by the delay time 350, is changed by shifting the phase by a very small amount of predetermined phase shift, in the phase compensation circuit 22. Then, a receive signal s3 can be generated, having the same waveform and phase as the receive signal s6 that is delayed by the delay time 351 being different from the delay time 350.

The phase compensation circuit 22 can reduce the scale of memory and the circuit size for the delay processing, as compared with the case of providing a second set of the delay circuit 121 and the summing circuit 123. Thus, in the ultrasound imaging apparatus of the present embodiment, while reducing the circuit size, the beamformed signal s4 can be generated, as in the case where the receive signal s1 is delayed by multiple delay times 350 and 351.

Specifically, the configuration of FIG. 2A of the present embodiment only requires finite number (between or equal to 2 and 100) of taps (stages of a digital filter) of the shift registers 41a and 41b and the interpolators 42a and 42b as shown in FIG. 4. In contrast, as in the comparative example of FIG. 2B, when a plurality of delay lines of another set of delay circuit 121 are prepared, memory buffer areas of 1,000 or more are required, corresponding to the total number of samples of one scanning line. Therefore, the configuration of FIG. 2A can achieve a circuit that enables generation of the beamformed signal s4 in much less implementation scale, as compared with the comparative example of FIG. 2B.

The phase shift amount of the phase compensation circuit 22 may vary in accordance with the change of the delay time 351 in the depth direction, and thus the receive signal s3 can be obtained at each depth of the receive focal point 20.

As described so far, in the present embodiment, the receive signals s2 and s3 can be generated by aligning the phases not only of the receive signals generated by the transmission beam 310, but also of the receive signals generated by any of the spherical waves such as the waves 301 to 306, or the waves such as the interference waves where some of the spherical waves are interfering. Thus, the receive beamformer 13 can obtain the beamformed signals s4 for the same receive scanning line, the beamformed signals s4 being affected by both the information of the receive signals s2 generated by the transmission beam 310, and the information of the receive signals s3 generated by any of the spherical waves 301 and others. Therefore, this allows obtainment of the beamformed signal with higher resolution, than the beamformed signal obtained only from the transmission beam 310.

The control unit 11 controls each part, with moving the transmission channels 105, in a manner that repeats transmitting and receiving until the beamformed signals of the receive scanning lines of the number necessary for image generation are obtained. This control method may be employed for a scanning type, such as linear scanning and convex scanning. In the case of sector (phased array) type scanning, though the transmission aperture is the same as the receiving aperture, there is employed a form such that a plurality of transmitting and receiving scanning lines are set on a two-dimensional plane by tilting the receive scanning line 36 in the angular direction, and imaging of a fan-shaped region is performed along the direction. For example, there is a form that 50 to 1,300 scanning lines are prepared in a ±45° or ±60° fan-shaped region about the center of the probe aperture. Also in this case, the control unit 11 controls each part in a manner that moves the angular direction of the transmission, instead of the transmission channels 105, and repeats transmitting and receiving until the beamformed signals of the receive scanning lines 36 of the number necessary for image generation can be obtained.

The imaging processor 15 generates an image from the beamformed signals of the number necessary for image generation, and displays the image on the image display unit 16 being connected. For example, the imaging processor 15 performs the following processing to generate an image; signal processing on the beamformed signals after the delay-and-sum processing, such as the digital filtering and interpolation processing, conversion processing to transform RF (Radio Frequency) signals to brightness signals, such as detection processing and envelope extracting processing, and image processing that performs sampling of each of the brightness signals generated from multiple beamformed signals, and further performs scan conversion (coordinate transformation) processing in accordance with the scanning method, to convert the brightness signals to signal intensity and brightness values for each pixel, whereby an image signals are generated and aligned to generate an image.

Figure 6:
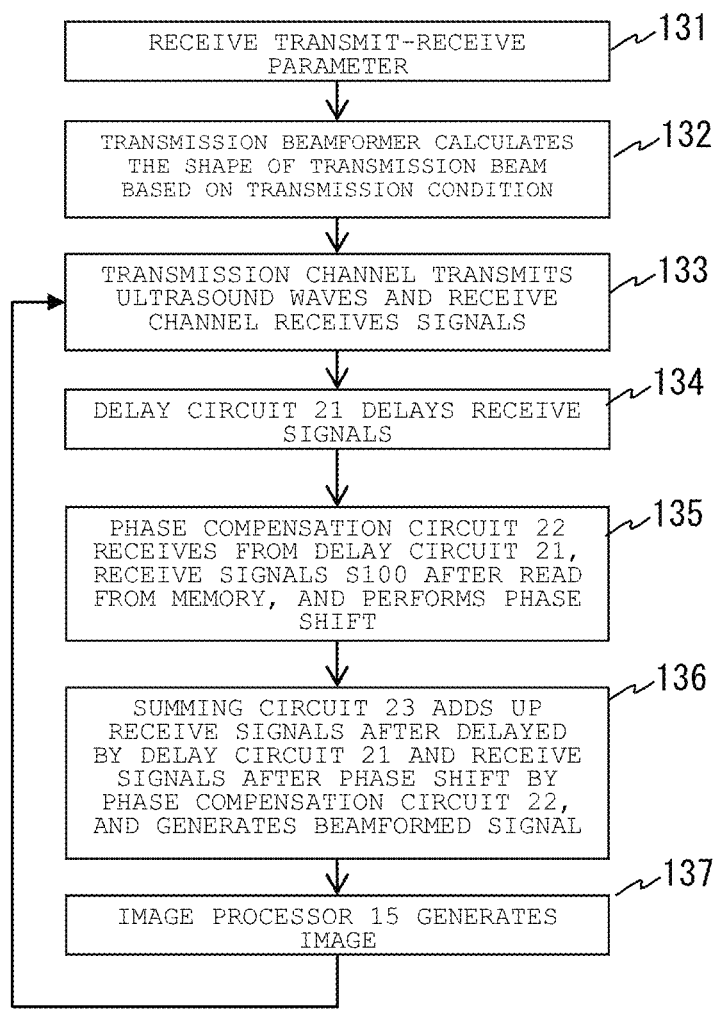
FIG. 6 is a flow diagram showing an operation of each unit of the ultrasound imaging apparatus during imaging according to the first embodiment.

Next, with reference to FIG. 6, there will be described an operation of each unit during the imaging by the ultrasound imaging apparatus of the present embodiment.

(Step 131)

First, the control unit 11 receives via the console 12, imaging condition parameters and/or transmit and receive parameters that are provided based on the imaging condition parameters, and/or a type of the connected ultrasound probe 116. The transmit and receive parameters include, for example, transmission aperture width, receive aperture width, frequency (center frequency, frequency band), a transmission focus position, a shape of transmission pulse wave (the number of waves and amplitude).

(Step 132)

The control unit 11 obtains the shape of the transmission beam 310 by calculation, on the basis of the condition and others received in step 131.

(Step 133)

The control unit 11 passes the transmission conditions such as the position of the transmission focus 30, transmission frequency, and transmission counts, to the transmission beamformer 14. The transmission beamformer 14 generates and outputs transmission signals to the ultrasound probe elements of the transmit channel 105 in the ultrasound element array 101. Each of the ultrasound probe elements of the transmission channel 105 transforms the transmission signals to an ultrasound wave, and then transmits the ultrasound wave. The receive channel 106 of the ultrasound probe element array 101 receives the sound wave from the subject, caused by the transmission in step 135, and outputs a receive signal s1.

(Step 134)

The delay circuit 21 once stores the receive signal s1 in the memory unit 21a, and the interpolation circuit 21b reads the receive signal s100 from the memory unit 21a at a timing of the clock frequency and delays the receive signal at a coarse temporal resolution. Then, the interpolation circuit 21b performs interpolation processing on thus readout receive signal s100, and further delays the receive signal at a higher temporal resolution equal to or less than the clock frequency, or not more than several times the wavelength, and outputs the receive signal s2. Thus, under the control of the control unit 11, the receive signal s1 can be delayed with the delay time provided from the delay time storage unit 19 to the interpolation circuit 21b, and a delayed receive signal s2 is generated.

(Step 135)

The phase compensation circuit 22 branches the receive signal s100 immediately after being outputted from the memory unit 21a in the delay circuit 21, further shifts the phase of the receive signal s100 after branched, thereby generating a phase-shifted receive signal s3. The phase shift amount is stored in advance in the phase shift amount storage unit 18, and the amount is a value set in the phase compensation circuit 22 from the phase shift amount storage unit 18, under the control from the phase compensation circuit control unit 17.

(Step 136)

The summing circuit 23 adds the delayed receive signal s2 in the delay circuit 21, to the phase-shifted receive signal s3 in the phase compensation circuit 22, to generate a beamformed signal s4.

(Step 137)

The imaging processor 15 performs the signal processing and the image processing on the beamformed signal s4 for each of the receive scanning lines.

Thus, in the present embodiment, not only the receive signal s2 generated by the transmission beam 310, but also the receive signal s3 can be generated by the phase shift, the receive signal s3 being equivalent to the receive signal generated from any of the spherical waves such as the waves 301 and 306 or the interference waves where some of the spherical waves are interfering. Thus, with a reduced circuit size and a smaller amount of calculation, the receive beamformer 13 can generate an image with high resolution, affected by both the information of the receive signal s2 generated by the transmission beam 310, and the information of the receive signal s3 generated by any of the spherical waves 301 and others.

(Modification 1-1: Multiple Receiving Scanning Lines)

There will be described a modified example of the ultrasound imaging apparatus of the first embodiment.

The ultrasound imaging apparatus of the present embodiment is not limited to a configuration that obtains the beamformed signal for one receive scanning line in one transmission. It is also possible to generate the beamformed signal for each of multiple receive scanning lines in one transmission. Thus, the number of transmissions required to generate one image is reduced, and this enables high-speed imaging.

(Modification 1-2: Synthetic Transmit Aperture)

Another modification of the ultrasound imaging apparatus of the first embodiment will be described.

The ultrasound imaging apparatus of the present embodiment may be configured such that the beamformed signal is generated for each of the multiple receive scanning lines in one transmission, and the transmission aperture is synthesized if necessary. In that case, the synthetic aperture synthesizer 15a is disposed in the imaging processor 15 as shown in FIG. 1.

The receive beamformer 13 generates the beamformed signal s4 for each of the multiple receive scanning lines with respect to the receive signal s1 obtained by one transmission.

The synthetic aperture synthesizer 15a stores in an incorporated memory, the beamformed signals s4 of the multiple receive scanning lines obtained for one transmission. The synthetic aperture synthesizer 15a adds up and synthesizes the beamformed signals s4 of the multiple receive scanning lines obtained by transmission, to the beamformed signals s4 of the receive scanning line obtained in the previous transmission, with respect to each receive scanning line at the same position, thereby obtaining a beamformed signal after aperture synthesis. The addition may be weighted addition.

The imaging processor 15 generate an image using the beamformed signals after aperture synthesis.

Thus, by performing the aperture synthesis, it is possible to generate an image with improved spatial resolution.

Since the present embodiment relates to the most upstream signal processing in the ultrasound apparatus, that is, the receive beamformer 13, it is possible to employ the present embodiment in combination not only with the transmission aperture synthesis, but also with other ultrasound imaging methods, for example, non-linear (harmonic) imaging, Doppler imaging, color flow imaging, coherence imaging, and imaging utilizing adaptive beamforming.

<Modification 1-3: Weighted Addition by Depth>

There will be described still another modification of the ultrasound imaging apparatus of the first embodiment.

When adding up the delayed receive signal s2 and the phase-shifted receive signal s3, the summing circuit 23 of the receive beamformer 13 may be configured to perform weighting before the addition. In that case, the control unit 11 may have the configuration that varies the weight used for the weighting by the summing circuit 23 in accordance with a range of the depth, thereby setting an appropriate weight to obtain a high-resolution image. Further, the control unit 11 may accept a weight provided by an operator via the console 12, or the control unit may change the weight according to the imaging conditions.

Second Embodiment

Figure 7:
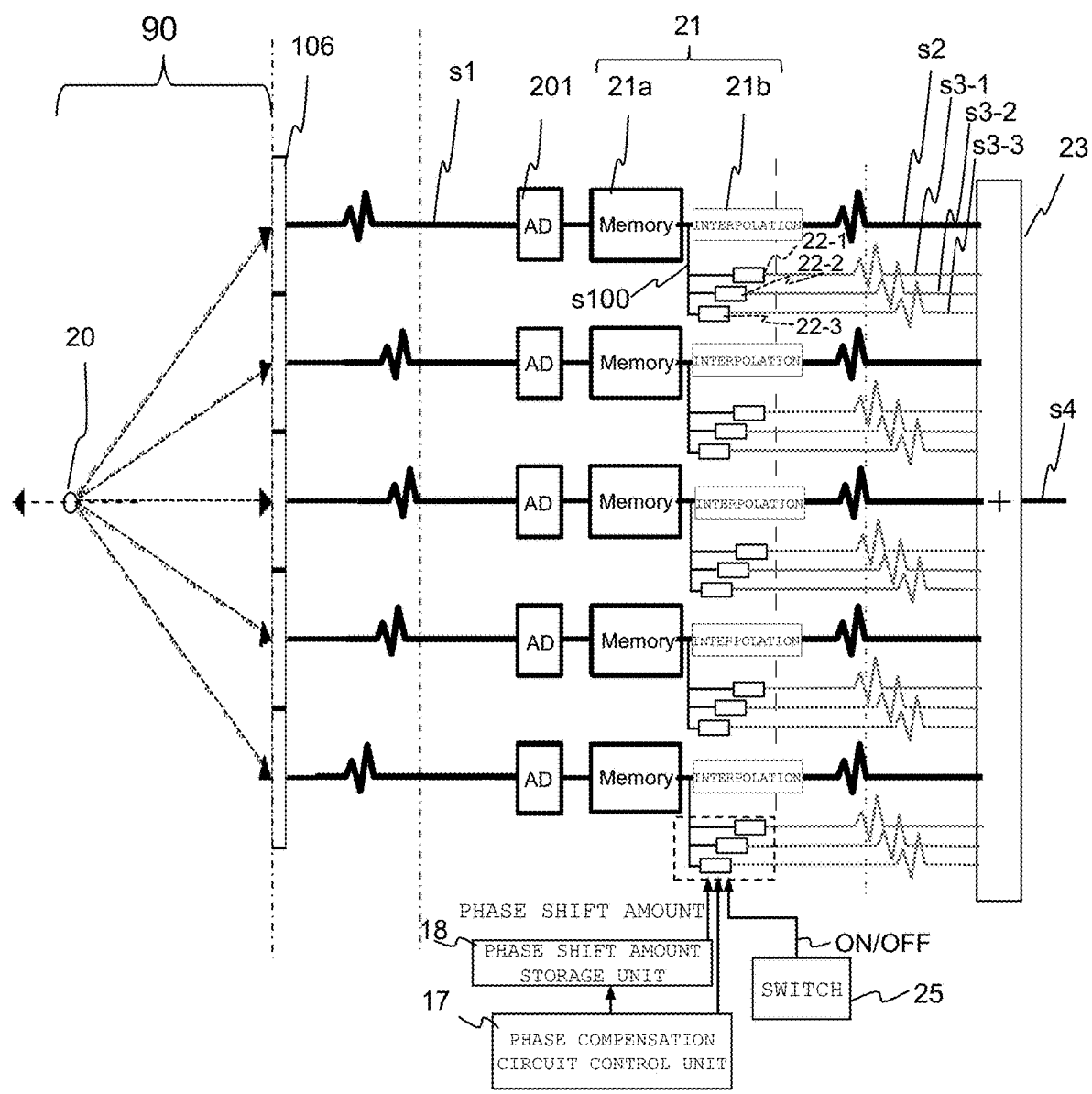
FIG. 7 is a block diagram showing the configuration of the receive beamformer according to the second embodiment.

With reference to FIG. 7, there will be described the ultrasound imaging apparatus according to the second embodiment. FIG. 7 shows a configuration of the receive beamformer 13 of the ultrasound imaging apparatus according to the second embodiment.

As shown in FIG. 7, in the receive beamformer 13 of the second embodiment, multiple phase compensation circuits 22-1, 22-2, and 22-3 are branched from the memory unit 21a and connected in the delay circuit 21, in order to obtain a beamformed signal affected by the receive signals from multiple spherical waves including the waves 301 to 306 or the interference waves of some of them.

The multiple phase compensation circuits 22-1, 22-2, and 22-3 branch the receive signal s100 outputted from the memory unit 21a into more than one signal, shifting the phase at different phase shift amounts respectively, to generate phase-shifted receive signals s3-1, s3-2, and s3-3. The summing circuit 23 adds up the receive signal s2 outputted from the interpolation circuit 21b, and the phase-shifted receive signals s3-1, s3-2, and s3-3, to generate the beamformed signal s4.

Figure 8:
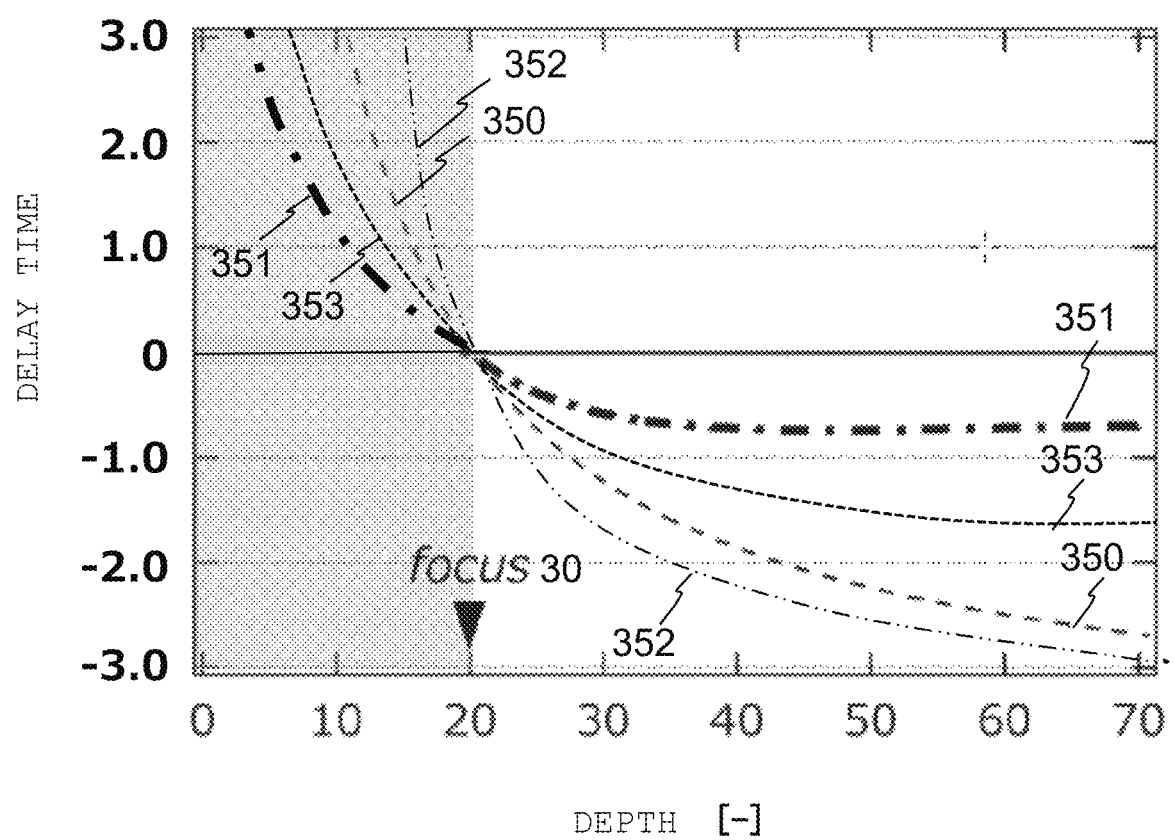
FIG. 8 is a graph showing an example of the delay curve representing the delay time with respect to the depth according to the second embodiment.

The phase shift amounts of the phase compensation circuits 22-1, 22-2, and 22-3 are set by the phase compensation circuit control unit 17, so that delays are performed being equivalent to the delays, as shown in FIG. 8, where the delay times 351, 352, and 353 are used for focusing the receive signals on the receive focal point 20, the receive signals being generated in the receive channels, respectively, by three types of waves among the multiple spherical waves such as 301 to 306 or interference waves where some of them are interfering.

Thus, it is possible to obtain the beamformed signal s4 affected by the receive signals generated not only from the transmission beam 310, but also from the multiple spherical waves such as 301 to 306 and the interference waves where some of them are interfering.

Further, in the present embodiment, the circuit size of one phase compensation circuit 22 is small, even when such multiple phase compensation circuits 22-1, 22-2, and 22-3 are placed, and thus it is possible to exert more control over the overall circuit size, than the case where a plurality of delay circuits 121 are disposed.

Descriptions of other configurations, operations, and effects will be omitted, because they are the same as the first embodiment.

(Modification 2-1: Weighted Addition)

There will be described a modification of the ultrasound imaging apparatus according to the second embodiment.

The summing circuit 23 of the receive beamformer 13 may be configured to perform addition after weighting, when adding up the receive signal s2 of the delay circuit 21, and the phase-shifted receive signals s3-1, s3-2, and s3-3 in the multiple phase compensation circuits 22-1, 22-2, and 22-3.

The control unit 11 may have the configuration that varies the weight used by the summing circuit 23 for weighting, in accordance with a range of the depth, thereby setting an appropriate weight to obtain a high-resolution image.

The control unit 11 may accept the weight set by an operator via the console 12, or change the weight according to the imaging conditions.

(Modification 2-2: Phase Shift Processing in Time Series)

There will now be described another modification of the ultrasound imaging apparatus according to the second embodiment.

The receive beamformer 13 is also capable of generating the phase-shifted receive signals s3-1, s3-2, and s3-3, by one phase compensation circuit 22 and memory, instead of the phase compensation circuits 22-1, 22-2, and 22-3. Specifically, the phase compensation circuit 22 repeats the following operation; generating the phase-shifted receive signal s3-1 by shifting the phase of the receive signal s100 in the delay circuit 21, then storing the signal in the memory, again, performing the phase shift on the receive signal s2 to generate the phase-shifted receive signal s3-2, and then storing the signal in the memory, and finally, the phase-shifted receive signals s3-1, s3-2, and s3-3 are stored in the memory. Further, the receive signal s2 without the phase shift is also stored in the memory. The summing circuit 23 reads from the memory, the receive signal s2, and the phase-shifted receive signals s3-1, s3-2, and s3-3, and adds up those signals.

In this configuration, since only one phase compensation circuit 22 is sufficient at least, and thus required circuit size can be small. It is therefore possible to mount the receive beamformer 13 inside the ultrasound probe 116.

Also for the ultrasound imaging apparatus of the second embodiment, similar to the ultrasound imaging apparatus of the modified examples 1-1, 1-2, and 1-3 of the first embodiment, it is possible to perform the followings; high-speed imaging by generating multiple receive scanning lines for one transmission, transmission aperture synthesis, and weighted addition by depth.

Third Embodiment

Figure 9:
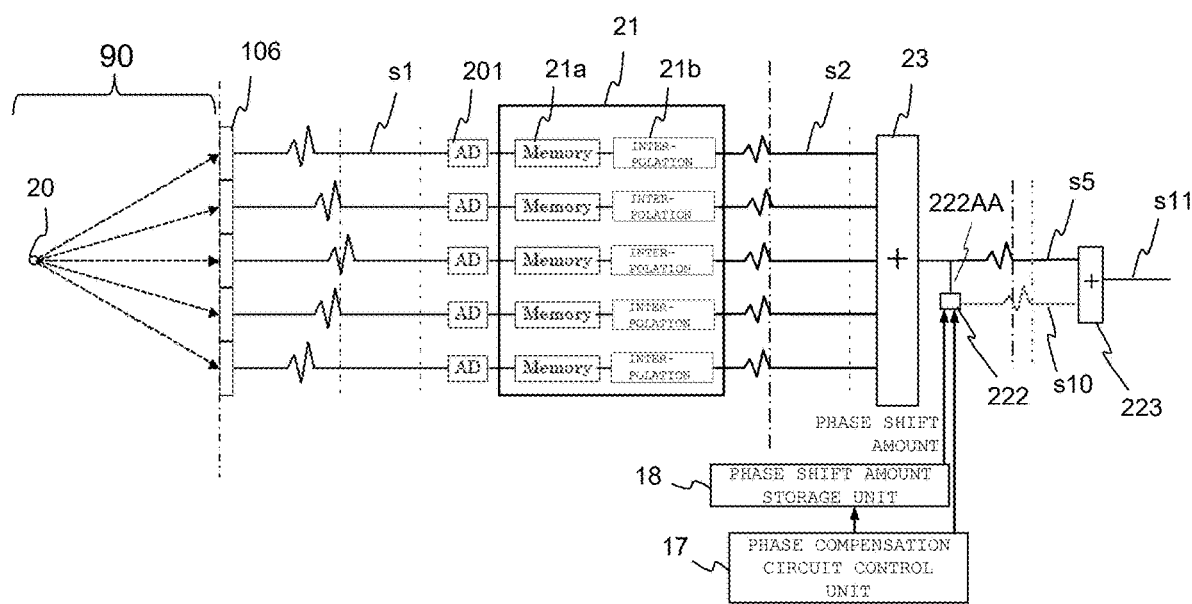
FIG. 9 is a block diagram showing the configuration of the receive beamformer according to a third embodiment.

With reference to FIG. 9, there will now be described the ultrasound imaging apparatus according to a third embodiment.

As shown in FIG. 9, the ultrasound imaging apparatus of the third embodiment has the configuration that the phase compensation circuit 222 and a summing circuit 223 are disposed in the subsequent stage of the summing circuit 23. After the summing circuit 23, in general, a memory is provided for storing beamformed signals. It is also possible, however, to process the outputted signals in time series, without providing the memory.

The phase compensation circuit 222 branches (via branching portion 222AA) the beamformed signal s5 outputted from the summing circuit 23 of the receive beamformer, performs the phase shift, and generates a phase-shifted beamformed signal s10. Further, the summing circuit 223 adds up the beamformed signal s5 outputted from the summing circuit 23, and the phase-shifted beamformed signal s10 outputted from the phase compensation circuit 222, and generates a beamformed signal s11.

The phase compensation circuit control unit 17 sets the amount of phase shift to the phase compensation circuit 222.

The imaging processor 15 generates an image using the beamformed signals s11 after the addition.

Descriptions of other configurations, operations, and effects will be omitted, since they are the same as the first embodiment.

In the third embodiment, by imparting the phased signal to the signal after subjected to the delay-and-sum processing, it is possible to significantly reduce the implementation scale as compared with the first embodiment. In the first embodiment, it is necessary to prepare the phase compensation circuits 22 the number of which corresponds to the number of channels, whereas in the second embodiment, it is only required to prepare one phase compensation circuit 222. For example, when the number of channels is 128, the implementation scale becomes approximately 1% or less, as compared with the first embodiment. In the first embodiment, rounding errors may occur due to interpolation processing in the multiple channels, and an effect of final image quality improvement may be lowered. In the third embodiment, on the contrary, the phase shift is performed only by one phase compensation circuit 222, and thus influence of the rounding errors can be minimized. Since it is impossible, however, to vary the amount of phase shift for each channel, as compared with the first embodiment, the degree of freedom in design and adjustment may be reduced.

It is of course possible to configure in the third embodiment, such that multiple phase compensation circuits 222 are arranged in parallel, as in FIG. 7 of the second embodiment, to generate multiple types of beamformed signals with different phase shift amounts, and the summing circuit 223 adds up those beamformed signals.

Also for the ultrasound imaging apparatus of the third embodiment, similar to the ultrasound imaging apparatus of Modifications 1-1, 1-2, and 1-3 of the first embodiment, it is possible to perform the followings; generation of multiple receive scanning lines for one transmission to perform high-speed imaging, transmission aperture synthesis, and weighted addition by depth in the summing circuit 223.

Fourth Embodiment

Figure 10:
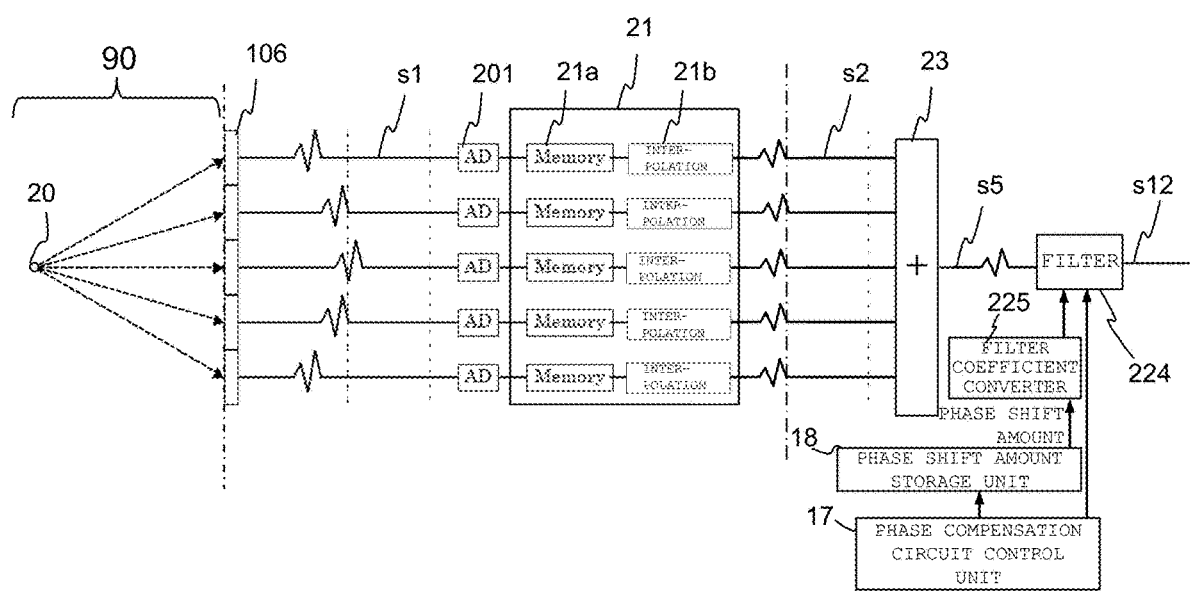
FIG. 10 is a block diagram showing the configuration of the receive beamformer according to a fourth embodiment.

With reference to FIG. 10, there will be described the ultrasound imaging apparatus according to a fourth embodiment.

As shown in FIG. 10, in the present embodiment, the digital filter 224 that is disposed subsequent to the summing circuit 23 adjusts a waveform of the beamformed signal s5 outputted from the summing circuit 23, and generates the beamformed signal s12 of the same waveform as the beamformed signal s11 outputted by the ultrasound imaging apparatus of the third embodiment. The digital filter 224 has a configuration including at least one of an adder, a multiplier, and a delayer, and adjusts the waveform by processing the beamformed signal s5 with these adder, multiplier, delayer, and others.

The digital filter 224 is connected to the filter coefficient converter 225. As the digital filter 224, either a digital FIR filter or a digital IIR filter may be used. The filter coefficient converter 225 receives the phase shift amount corresponding to the depth of the receive focal point, from the phase shift amount storage unit 18, and in accordance with the phase shift amount, the filter coefficient converter changes filter coefficients (values of the weight to be multiplied at each tap of the digital filter) such as a multiplication coefficient and a delay coefficient of the digital filter 224.

Specifically, as shown in FIG. 10, the filter coefficient converter 225 converts the phase information outputted from the phase shift amount storage unit 18 (the amount of phase shift), into a filter coefficient of the digital filter 224, and imparts a change to the filter coefficient that has been prepared in advance by the ultrasound imaging apparatus. The filter coefficient thus changed is transferred to the digital filter 224, and it is set therein. The digital filter 224 processes the waveform of the beamformed signal s5 with the changed filter coefficient to generate the beamformed signal s12. Then, the signal processing equivalent to the first embodiment can be performed according to the filtering.

At this time, similarly to the first embodiment, the phase compensation circuit control unit 17 instructs the phase shift amount storage unit 18 to output a corresponding amount of phase shift, as well as instructing the filter coefficient converter to performs the equivalent conversion processing in association with the amount of phase shift.

That is, according to the filter control, the ultrasound imaging apparatus of the fourth embodiment can generate the beamformed signal S12 being the same beamformed signal as the first embodiment or the third embodiment.

Descriptions of other configurations, operations, and effects of the ultrasound imaging apparatus of the fourth embodiment will be omitted, because they are the same as the first embodiment. Further, the ultrasound imaging apparatus of the fourth embodiment employs the digital filter 224, thereby simultaneously achieving not only the effect of the ultrasound imaging apparatus according to the first embodiment, but also the effect obtained by the ultrasound imaging apparatus comprising multiple phase compensation circuits according to the second embodiment. In order that the ultrasound imaging apparatus using the digital filter 224 of the fourth embodiment achieves an effect equivalent to the effect of the ultrasound imaging apparatus of the second embodiment with a large number of lines such as the phase compensation circuit 22-1 and others, it is only required to increase the numbers of taps (stages) of the filter coefficient of the digital filter 224. Thus, it is possible to generate the filter coefficient (an array of filter coefficients) having an effect equivalent to the effect of the multiple phase compensation circuits 22-1 and others of the second embodiment.

The phase shift processing by the filtering process of the digital filter 224 of the ultrasound imaging apparatus according to the fourth embodiment is implemented on software running on a CPU or GPU rather than hardware. Therefore, the circuit size of the hardware can be minimized. Further, a filter block already provided in the ultrasound imaging apparatus, such as a variable depth filter, may also function as the digital filter 224 to implement the phase shift processing, and therefore this can increase a degree of freedom in adjustment of design.

Fifth Embodiment

With reference to FIGS. 1, 7, and 11 to 13, the ultrasound imaging apparatus of the fifth embodiment will be described.

Though the configuration of the ultrasound imaging apparatus according to the fifth embodiment is the same as the first or second embodiment, the number of generated phase-shifted receive signals is made different in accordance with the depth range of the subject 90.

Figure 11:
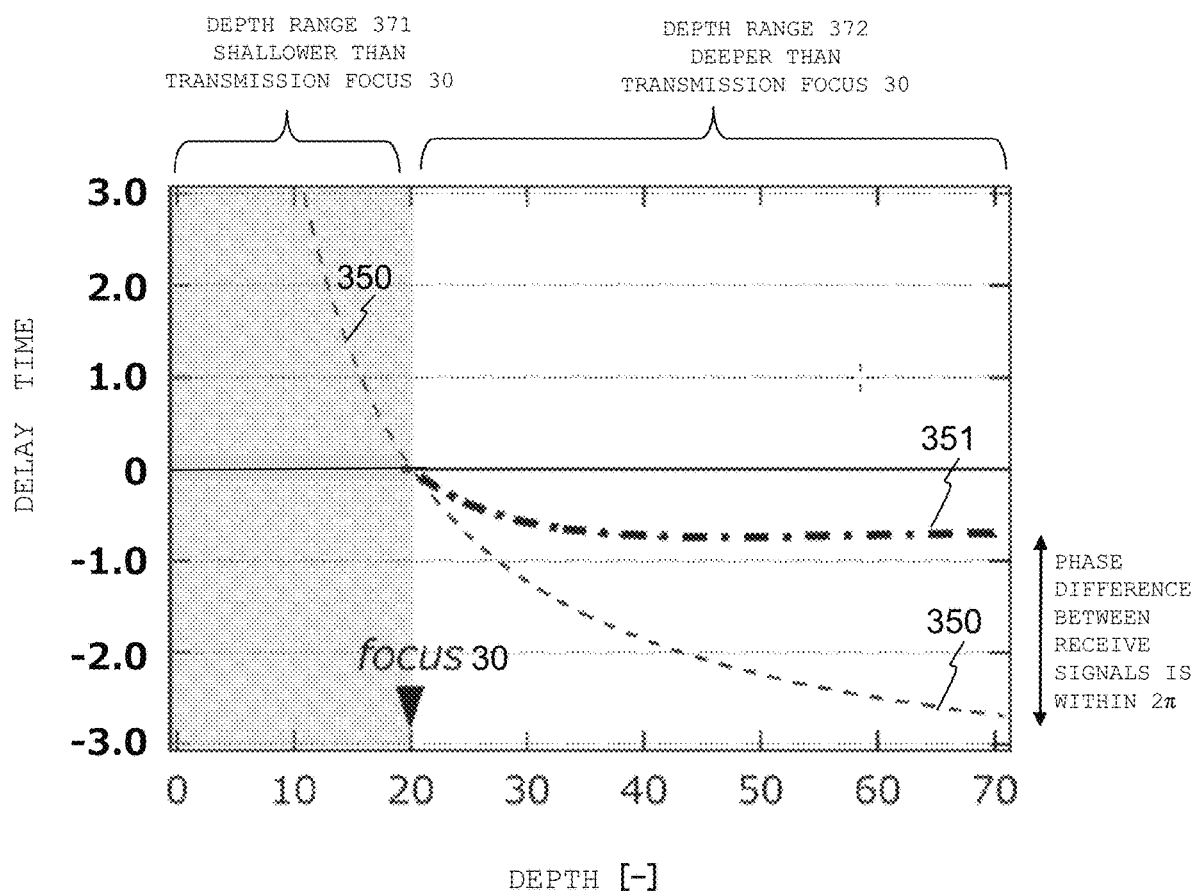
FIG. 11 is a graph showing an example of the delay curve representing the delay time with respect to the depth according to a fifth embodiment.
Figure 12:
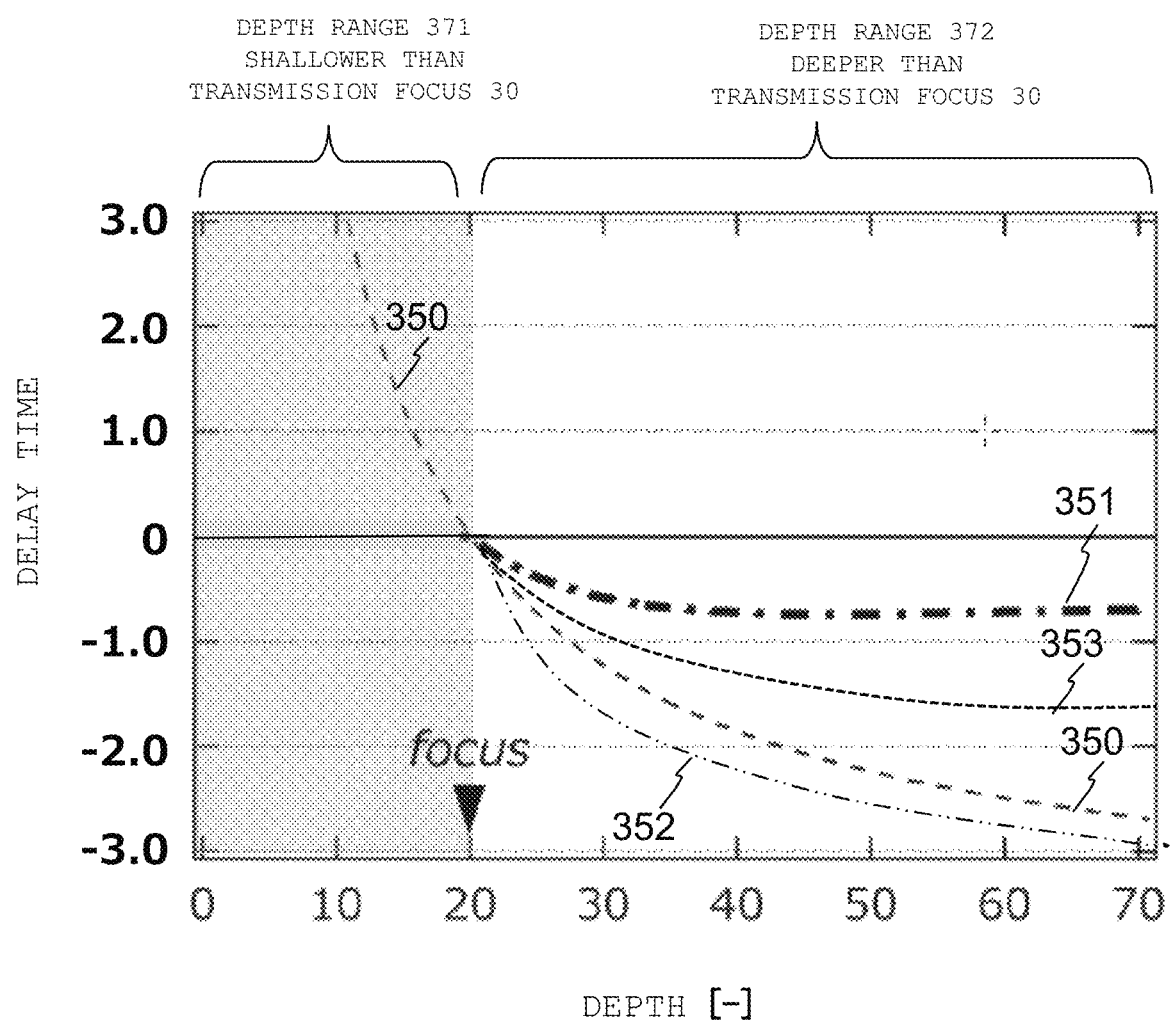
FIG. 12 is a graph showing an example of the delay curve representing the delay time with respect to the depth according to the fifth embodiment.

For example, as shown in FIGS. 1 and 7, there are provided the phase compensation circuit 22 and the switch 25 for turning on and off the phase compensation circuits 22-1, 22-2, and 22-3, and the control unit 11 turns off the phase compensation circuit 22 and the phase compensation circuits 22-1, 22-2, and 22-3 according to the depth of the subject 90. Thus, for example, as shown in FIGS. 11 and 12, in the depth range 371 placed shallower than the transmission focus 30, the phase compensation circuit 22 of FIG. 1, and the phase compensation circuits 22-1, 22-2, 22-3 of FIG. 7 are not operated by turning off by the switch 25. In the depth range 372 placed deeper than the transmission focus 30, the phase compensation circuit 22 and the phase compensation circuits 22-1, 22-2, and 22-3 are operated by turning on by the switch 25. Accordingly, receive signals are generated being similar to the receive signals obtained by delaying the receive signals of the spherical waves 301 and others respectively by the delay time 351 or the delay times 351, 352, and 353, affecting the beamformed signal s4.

Thus, it is possible to obtain a high-resolution image of the range deeper than the transmission focus 30, while reducing the calculation amount of the phase compensation circuit 22.

Turning the switch 25 on and off enables that the number of phase-shifted receive signals generated in the depth range 371 shallower than the transmission focus 30 is made larger than the number of phase-shifted receive signals generated in the depth range 372 deeper than the transmission focus 30. As shown in FIG. 13, this allows generation of receive signals which are equivalent to the receive signals delayed by the delay times 350 to 353 in the portion shallower than the transmission focus 30, and the receive signals delayed by the delay times 351 to 352 in the portion deeper than the transmission focus 30.

For example, the depth range is obtained in advance, where increase of the number of phase-shifted receive signals generated by the phase compensation circuit 22 is effective for improving the resolution, for each imaging target site (abdomen, circulatory organ, thorax, leg, blood vessel, digestive organ, pregnant woman screening, and others) and for each imaging target organ (liver, heart, kidney, pancreas, gallbladder, ovary, carotid artery, thyroid, and others). Then, the control unit 11 is only required to turn on the phase compensation circuit 22 by the switch 25 in the depth range. Selection of the site or the organ is accepted from the operator via the console 12 which is connected to the control unit 11.

Further, the control unit 11 may accept from the operator via the console 12, the depth range where high-resolution imaging is desired, to increase the number of the phase compensation circuits 22 to be turned on in the depth range. Alternatively, the phase compensation circuit 22 may be turned on in advance in a predetermined depth range.

Furthermore, the control unit 11 may incorporate a machine learning model, and input into the machine learning model, various parameters related to ultrasound imaging such as imaging condition parameters, transmit and receive parameters, and types of the probe, and ultrasound images obtained in advance as a preparation before actual imaging or receive signals of such ultrasound images, thereby calculating the appropriate number of the phase-shifted receive signals, and/or calculating for each depth, the phase shift amount in accordance with the depth.

The machine learning model to be employed has learned in advance, using as input data, imaging conditions, captured images or receive signals, and phase-shifted receive signals used in the image generation, and as correct data, resulting images, the number of phase-shifted receive signals, and the phase shift amounts.

Further, since accuracy and resolution of the imaging may differ depending on the types of organ, the machine learning model as described above may be the model that has learned separately organ by organ, such as liver, kidney, blood vessels, mammary glands, and others.

In the above-described first to fifth embodiments, the receive beamformer 13 can be configured by hardware. For example, a custom-made IC such as ASIC (Application Specific Integrated Circuit) or a programmable IC such as FPGA (Field-Programmable Gate Array) may be used to design the circuit so as to implement the functions of each part. It is also possible to implement some or all of the functions of the receive beamformer 13 by software. In that case, the receive beamformer 13 is constructed by devices such as a computer, equipped with processors including CPU (Central Processing Unit) or GPU (Graphics Processing Unit) and a memory, and the CPU reads and executes the programs stored in the memory, thereby implementing the functions of those devices.

Description of Effects of Embodiments

With reference to FIGS. 14A to 14E, there will be described the effects of the present embodiments. FIG. 14A is an ideal point image representing a desirable image when an image of a phantom containing a minute spherical object was obtained. FIG. 14B is an ultrasound image obtained by imaging the same phantom as FIG. 14A employing the ultrasound imaging apparatus that used conventional delay times (the delay curve of the delay time per receive scanning line is one) (Comparative Example).

FIG. 14C is an image of the same phantom as FIG. 14A, obtained by using the ultrasound imaging apparatus of the first embodiment where the receive signal s2 obtained in the delay time 350 of FIG. 5 and the receive signal s3 obtained by the phase shift were added up by the summing circuit 23, showing the ultrasound image generated from the resulting beamformed signals s4. The amount of phase shift of the receive signal s3 with respect to the receive signal s2 was within one wavelength. It has been found from the ultrasound image of FIG. 14C, as compared with the ultrasound image of FIG. 14B of the comparative example, that the side lobe and noise components due to diffracted waves around the point were reduced, and the obtained image became closer to the ideal point image.

Similar to FIG. 14C, the ultrasound images of FIG. 14D and FIG. 14E were obtained by the same apparatus as the ultrasound imaging apparatus of the first embodiment, and the phase shift amount of the receive signal s3 was set to be more than several times the wavelength with respect to the receive signal s2. In the ultrasound image of FIG. 14D, the phase shift amount was so large that artifact imaging occurred in a different location, and in the ultrasound image of FIG. 14E, the point image was split.

Thus, according to the ultrasound imaging apparatus of the present embodiment, it is possible to obtain an ultrasound image of higher resolution than the comparative example, while preventing artifacts. It is also found that preferably the phase shift amount should be within one wavelength ($2\pi$ rad).

What is claimed is:

1. An ultrasound imaging apparatus comprising:
    an ultrasound element array including a plurality of ultrasound elements arranged in an array;
    a transmission beamformer configured to output a transmission signal to each of the ultrasound elements of the ultrasound element array, thereby causing the ultrasound elements to transmit ultrasound waves delayed by a phase of a predetermined amount to a subject, focusing the ultrasound waves at a predetermined transmission focus;
    a phase compensation circuit control unit; and
    a receive beamformer configured to perform receive beamforming on receive signals, the receive beamformer including
        a plurality of delay circuits, each delay circuit being configured to receives a corresponding receive signal that is output by a corresponding ultrasound element of the ultrasound elements receiving the ultrasound waves reflected by the subject that has received the ultrasound waves, and to delay the receive signal by a delay time that is predetermined for the ultrasound element according to a receive focal point of the subject,
        a plurality of phase compensation circuits, each phase compensation circuit being configured to shift the phase of the receive signal by a phase shift amount specified by the phase compensation circuit control unit, and to output a phase-compensated receive signal,
        a plurality of branching portions, each branching portion being configured to branch a corresponding signal line of the corresponding receive signal input to the corresponding delay circuit from the corresponding ultrasonic element, and to connect the branched signal line to the phase compensation circuit, and
        a summing circuit configured to sum (i) a delayed receive signal output from each of the plurality of delay circuits and (ii) the phase-compensated receive signal output from each of the plurality of phase compensation circuits, and to generate a beamformed signal.

2. The ultrasound imaging apparatus according to claim 1, wherein
    the plurality of delay circuits include front-stage delay circuits each configured to perform delay processing with a coarse time resolution on the receive signal output by the corresponding ultrasonic element, and the plurality of delay circuits further include latter-stage delay circuits each configured to perform delay processing with a finer time resolution than the coarse time resolution of the front-stage delay circuit,
    the receive signal delayed with the coarse time resolution by the front-stage delay circuit is provided to the corresponding latter-stage delay circuit via the signal line from which the corresponding branching portion branches, and
    the phase compensation circuit is further configured to shift the phase of the receive signal delayed with the coarse time resolution by the phase shift amount specified by the phase compensation circuit control unit.

3. The ultrasound imaging apparatus according to claim 2, further comprising
    a plurality of A/D converters each disposed between a corresponding ultrasound elements 106 and a corresponding front-stage delay circuit of the front-stage delay circuits, wherein
    the front-stage delay circuit comprises a memory configured to temporarily store receive signals, and
    each of the delay circuits comprises
        a shift register configured to adjust a timing of reading out the receive signal from the memory, the receive signal read out from the memory being delayed and processed with the coarse time resolution, the shift register finely shifting a time of the receive signal read from the memory, and
        an interpolator configured to perform an interpolation process on the receive signal time-shifted by the shift register, thereby realizing the delay process with the fine time resolution.

4. An ultrasound imaging apparatus comprising:
    an ultrasound element array including a plurality of ultrasound elements arranged in an array;
    a transmission beamformer configured to output a transmission signal to each of the ultrasound elements of the ultrasound element array, thereby causing the ultrasound elements to transmit ultrasound waves each delayed by a corresponding phase of a predetermined amount to a subject, focusing the ultrasound waves at a predetermined transmission focus;
    a phase compensation circuit control unit; and
    a receive beamformer configured to perform receive beamforming on receive signals, the receive beamformer including
        a plurality of delay circuits, each delay circuit being configured to receives a corresponding receive signal that is output by a corresponding ultrasound element of the ultrasound elements receiving the ultrasound waves reflected by the subject that has received the ultrasound waves, and to delay the receive signal by a delay time that is predetermined for the ultrasound element according to a receive focal point of the subject,
        a first summing circuit configured to add the delayed receive signal output from each of the delay circuits to generate a first beamformed signal,
        a phase compensation circuit,
        a branch portion to branch a signal line through which the first beamformed signal generated by the first summing circuit passes, and to connect the branched signal line to the phase compensation circuit, the first beamformed signal being input to the phase compensation circuit through the signal line branched by the branch portion, and the phase compensation circuit shifting a phase of the first beamformed signal by a phase shift amount specified by the phase compensation circuit control unit and supplying a phase-shifted beamformed signal, and
        a second summing circuit configured to add (i) the first beamformed signal generated by the first summing circuit and (ii) the phase-shifted beamformed signal the phase of which has been shifted by the phase compensation circuit, to generate a second beamformed signal.

5. The ultrasound imaging apparatus according to claim 1, wherein
the phase shift amount is within one wavelength of the ultrasound waves transmitted by the ultrasound elements.

6. The ultrasound imaging apparatus according to claim 1, wherein
two or more of the phase compensation circuits are arranged for each of the delay circuits, and
the two or more of the phase compensation circuits have different phase shift amounts, shift the receive signals delayed by the delay circuit by the phase shift amounts different from each other to generate two or more types of the phase-compensated receive signals, and then, add up the two or more types of phase-compensated receive signals being generated and the receive signal or the beamformed signal before branched.

7. The ultrasound imaging apparatus according to claim 1, further comprising a switch configured to switch whether or not the phase compensation circuit is to be operated, according to a depth of the receive focal point from a skin of the subject.

8. The ultrasound imaging apparatus according to claim 6, further comprising a switch configured to switch a number of phase compensation circuits to be operated among the two or more of the phase compensation circuits, according to a depth of the receive focal point from a skin of the subject.

9. The ultrasound imaging apparatus according to claim 1, wherein
the phase compensation circuit generates the phase-compensated receive signal, only in the case where a depth of the receive focal point from a skin of the subject falls within a predetermined range.

10. The ultrasound imaging apparatus according to claim 1, wherein
the phase shift amount of the phase compensation circuit varies according to a depth of the receive focal point from a skin of the subject.

11. The ultrasound imaging apparatus according to claim 9, further comprising a phase shift amount storage unit configured to store in advance the phase shift amounts respectively for the depths of the receive focal points, wherein
the phase compensation circuit shifts the phase of the receive signal by the phase shift amount stored in the phase shift amount storage unit in association with the depth of the receive focal point.

12. The ultrasound imaging apparatus according to claim 1, wherein
the receive beamformer comprises a memory, and
the receive beamformer generates, for one transmission from the transmission beamformer, the beamformed signal as to each of multiple receive focal points on multiple receive scanning lines, and stores the beamformed signal in the memory; and the receive beamformer generates for a second transmission, the beamformed signal as to each of multiple receive focal points on multiple receive scanning lines; and then, the receive beamformer synthesizes for a receive scanning line on a same position among the multiple receive scanning lines, the beamformed signals thus generated, with the beamformed signals already stored in the memory, to perform synthetic transmit aperture.

13. A signal processing method for an ultrasound imaging apparatus to process receive signals and output from an ultrasound element array including plural ultrasound elements, after transmitted ultrasound wave is returned to the ultrasound element array from a subject that received the transmitted ultrasound wave, comprising:
delaying by plural delay circuits of the ultrasound imaging apparatus the receive signals by delay amounts that are predetermined for the ultrasound elements according to depths of the receive focal points from a skin of the subject;
branching the receive signals from the delay circuits; and generating, for each branched receive signal of the branched receive signals, a phase-compensated receive signal obtained by shifting a phase of the branched receive signal by a phase shift amount; and
generating a beamformed signal by adding the phase-compensated receive signals and the delayed receive signals.

14. A signal processing method for an ultrasound imaging apparatus to process receive signals and output from an ultrasound element array including plural ultrasound elements, after transmitted ultrasound wave is returned to the ultrasound element array from a subject that received the transmitted ultrasound wave, comprising:
delaying by plural delay circuits of the ultrasound imaging apparatus the receive signals by delay amounts that are predetermined for the ultrasound elements according to depths of the receive focal points from a skin of the subject, and generating a first beamformed signal by adding the delayed receive signals output from the plural delay circuits;
branching the first beamformed signal to a branched signal line, and shifting a phase of the beamformed signal on the branched signal line by a predetermined phase shift amount to generate a phase-compensated beamformed signal; and
adding the first beamformed signal and the phase-compensated beamformed signal, to generate a second beamformed signal.

* * * * *